United States Patent

Merger et al.

Patent Number: 5,554,787
Date of Patent: Sep. 10, 1996

[54] 2,2-DIALKYLPENTANE 1,5-DIISOCYANATES, 2,2-DIALKYLPENTANE 1,5-DIURETHANES AND 2,2-DIALKYLPENTANE 1,5-DICARBAMOYL CHLORIDES, AND THEIR PREPARATION AND USE

[75] Inventors: Franz Merger; Andreas Otterbach, both of Frankenthal; Tom Witzel, Ludwigshafen; Hans Renz, Meckenheim, all of Germany

[73] Assignee: BASF Aktiengesellschaft, Ludwigshafen, Germany

[21] Appl. No.: 383,771

[22] Filed: Feb. 3, 1995

Related U.S. Application Data

[63] Continuation of Ser. No. 655,471, Feb. 14, 1991, abandoned.

[30]    Foreign Application Priority Data

Mar. 30, 1990 [DE] Germany .................. 40 10 226.2

[51] Int. Cl.⁶ ................................. C07C 265/04
[52] U.S. Cl. ...................................... 560/355
[58] Field of Search ............................... 560/355

[56]         References Cited

U.S. PATENT DOCUMENTS

| 2,784,163 | 3/1957 | Reynolds | 560/158 |
|---|---|---|---|
| 2,865,940 | 12/1958 | Nubis | 560/158 |
| 3,691,134 | 9/1972 | Feldman et al. | |
| 4,759,832 | 7/1988 | Degner | 560/115 |

OTHER PUBLICATIONS

Jerry March, "Reactions, Mechanisms, and Structure," Advanced Organic Chemistry, 3rd Edition, New York, pp. 237–241. 1985.
Ernest L. Eliel, "Stereochemistry of Carbon Compounds," McGraw-Hill, 1962, pp. 87–179.
Justus Liebigs Annalen Der Chemie, vol. 562, pp. 6, 84–88, 122–124, 1949.

*Primary Examiner*—Samuel Barts
*Attorney, Agent, or Firm*—Dennis V. Carmen

[57]            ABSTRACT

Novel 2,2-dialkylpentane-1,5-diisocyantes, 2,2-dialkylpentane-1,5-diurethanes and 2,2-dialkylpentane-1,5-dicarbamoyl chlorides of the formula $$X-CH_2-\underset{\underset{R^2}{|}}{\overset{\overset{R^1}{|}}{C}}-CH_2-CH_2-CH_2-X$$

where $R^1$ and $R^2$ are identical or different linear $C_1$- to $C_{12}$-alkyl, branched $C_3$- to $C_{12}$-alkyl, branched $C_2$- to $C_{12}$-alkenyl or branched $C_4$- to $C_{12}$-alkenyl, or $R^1$ and $R^2$ together are alkylene having from 4 to 7 carbon atoms, which is unsubstituted or substituted by from 1 to 5 $C_1$- to $C_4$-alkyl groups, and X is NCO, NH—$CO_2R^3$, $NHCO_2R^4$ or NHCOCl, where $R^3$ and $R^4$ are identical or different and are linear $C_1$- to $C_{20}$-alkyl, branched $C_3$- to $C_{20}$-alkyl or $C_5$- to $C_{12}$-cycloalkyl, are described.

1 Claim, No Drawings

2,2-DIALKYLPENTANE 1,5-DIISOCYANATES, 2,2-DIALKYLPENTANE 1,5-DIURETHANES AND 2,2-DIALKYLPENTANE 1,5-DICARBAMOYL CHLORIDES, AND THEIR PREPARATION AND USE

This is a continuation of application Ser. No. 07/655,471 filed Feb. 14, 1991, now abandoned.

The present invention relates to novel 2,2-dialkylpentane 1,5-diisocyanates, and to their preparation and use, preferably for the production of compact or cellular plastics by the polyisocyanate polyaddition process, and to 2,2-dialkylpentane-1,5-diurethanes and 2,2-dialkylpentane-1,5-dicarbamoyl chlorides, which are suitable, for example, as starting materials for the preparation of the 2,2-dialkylpentane 1,5-diisocyanates or of high-molecular-weight polycondensation products and are pesticides. For simplification, the description usually refers only to 2,2-"dialkyl" pentane groups, although for the purposes of the invention this term equally refers to 2,2-dialkenylpentane and 2-alkyl-2-alkenylpentane groups and 1-methylene-1-propylenecycloalkylene radicals having from 5 to 8 carbon atoms.

Organic, for example aliphatic, cycloaliphatic or aromatic, polyisocyanates have been disclosed in numerous patents and publications, e.g. by Werner Siefken, Ann. 562 (1949), 75–136, and are preferably used as highly reactive intermediates and starting materials for the preparation of urethane-, urea- and/or isocyanurate-containing high-molecular-weight polyaddition products. Of particular importance in large-scale industry are the (cyclo)aliphatic diisocyanates 1,6-hexamethylene diisocyanate and 1-isocyanato-3-isocyanatomethyl-(3,5,5-trimethyl)cyclohexane (isophorone diisocyanate) as starting components for fibers, adhesives and light- and thermostable coatings and paints, and the aromatic polyisocyanates 1,5-naphthylene diisocyanate as starting materials for compact or cellular elastomers and casting resins, 2,4- and 2,6-tolylene diisocyanate and mixtures thereof and/or mixtures of diphenylmethane diisocyanates and polyphenylpolymethylene polyisocyanates as starting materials for soft/elastic, semihard or hard polyurethane foams or isocyanurate- and urethane-containing hard foams, and 4,4'-diphenylmethane diisocyanate as a starting material for fibers, adhesives and thermoplastic polyurethanes.

In addition, many patent specifications describe specific preparation processes for organic polyisocyanates or specific organic polyisocyanates for specific areas of application.

For example, U.S. Pat. No. 3,311,654 describes the preparation of organic isocyanates, for example monoisocyanates, diisocyanates and polyfunctional polyisocyanates by pyrolysis of secondary carbamoyl chlorides. DE-C-28 30 243 describes aliphatic, branched, long-chain diisocyanates, namely 1,9-diisocyanato-5-methylnonane and 1,8-diisocyanato-2,4-dimethyloctane, as suitable diisocyanates for coil coating paints. Polysubstituted 1,5-pentane diisocyanates containing a stearically hindered isocyanate group, of the formula $$OCN\text{---}CHR^1\text{---}CR^2R^3\text{---}CH_2\text{---}CHR^4\text{---}CH_2\text{---}NCO,$$

where, inter alia, $R^1$ is $C_1$- to $C_{10}$-alkyl, phenyl or alkoxyalkylene, are disclosed in EP-B-077 105 and are used in paint systems having an extended pot life.

Isocyanatouretdiones, which are prepared by dimerizing 2-methylpentane 1,5-diisocyanate or 2-ethylbutane 1,4-diisocyanate and can be pyrolyzed back to more than 70%, are disclosed in DE-A-32 27 779 (U.S. Pat. No. 4,668,780). The modified diisocyanates are used, in particular, in solvent-containing or solvent-free single- and two-component paints, for example coil coating paints, high solids paints and polyurethane powder coatings. 2-Methylpentane 1,5-diisocyanate, which is suitable as a starting material, is prepared, for example according to U.S. Pat. No. 3,631,198, from 1,5-diamino-2-methylpentane by phosgenation in a low-molecular-weight dialkyl phthalate as solvent. Furthermore, EP-A-261 604 (U.S. Pat. No. 4,748,226) describes 2-alkoxymethylpentane 1,5-di-isocyanates, which can be matched to the application and processing conditions by suitably modifying the alkoxymethyl group. Said publications do not describe 2,2-dialkylpentanel,5-diisocyanates, 2,2-dialkylpentane-1,5-diurethanes and 2,2-dialkylpentane-1,5-dicarbamoyl chlorides or a suitable process for their preparation.

It is an object of the present invention to provide novel pentane diisocyanates which can be modified, through suitable choice of substituents, with respect to their physical properties and processability and can affect the mechanical properties of the polyisocyanate polyaddition products produced therefrom, and, as 2,2-dialkylpentane-1,5-diurethanes or -1,5-dicarbamoyl chlorides, may be effective as pesticides. It should be possible to prepare the products simply and inexpensively.

We have found that this object is achieved by 2,2-dialkylpentane 1,5-diisocyanates of the formula (I)

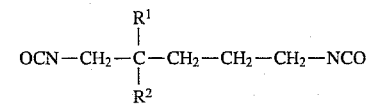

where $R^1$ and $R^2$ are identical or different and are linear $C_1$- to $C_{12}$-alkyl, preferably $C_1$- to $C_9$-alkyl, branched $C_3$- to $C_{12}$-alkyl, preferably $C_3$- to $C_8$-alkyl, linear $C_2$- to $C_{12}$-alkenyl, preferably $C_2$- to $C_9$-alkenyl, or branched $C_4$- to $C_{12}$-alkenyl, preferably $C_4$- to $C_8$-alkenyl, or $R^1$ and $R^2$ together are alkylene having from 4 to 7 carbon atoms, preferably 4 or 5 carbon atoms, or alkylene having from 4 to 7 carbon atoms, preferably 4 or 5 carbon atoms, which are substituted by from one to 5, preferably one or 2, $C_1$- to $C_4$-alkyl groups, preferably $C_1$- to $C_3$-alkyl groups.

Diisocyanates of the formula (I) which have proven particularly successful and are therefore preferred are those where $R^1$ and $R^2$ are identical or different and are selected from alkyl, e.g. methyl, ethyl, n-propyl, isopropyl, n-butyl, isobutyl, sec-butyl, 2-methylbutyl, n-pentyl, neopentyl, 2-methylpentyl, n-hexyl, 2-ethylhexyl, n-octyl, n-decyl and n-dodecyl, alkenyl, e.g. propenyl, 1- or 2-butenyl, 1-hexenyl, 1-octenyl and 2-vinyloctyl, and alkylene, e.g. butylene, pentylene and hexylene.

Examples of preferred 2,2-dialkylpentane 1,5-diisocyanates are 2,2-diethyl-, 2,2-dipropyl-, 2,2-dibutyl-, 2,2-dihexyl-, 2,2-dioctyl-, 2,2-diisopropyl-, 2-methyl-2-ethyl-, 2-methyl-2-n-propyl-, 2-methyl-2-isopropyl-, 2-ethyl-2-propyl-, 2-ethyl-2-butyl-, 2-ethyl-2-hexyl-, 2-ethyl-2-octyl-, 2-ethyl-2-decyl-, 2-methyl-2-propenyl- and 2-ethyl-2-butenylpentane 1,5-di-isocyanates and 1-(3-isocyanatopropyl)-1-isocyanatomethylcycloheptane and -cyclooctane. Particular preference is given to 2-methyl-2-propyl-, 2-ethyl-2-butyl- and 2-methyl-2-n-nonylpentane 1,5-diisocyanate and 1-(3-isocyanatopropyl)- 1-isocyanatomethylcyclopentane and -cyclohexane.

The 2,2-dialkylpentane 1,5-diisocyanates of the formula (I) are obtainable by pyrolysis of 2,2-dialkyl-pentane- 1,5- dicarbamoyl chloride of the formula (III)

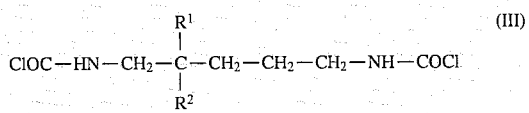

where
R¹ and R² are as defined above, in the presence of an organic solvent which is inert toward NCO groups under the reaction conditions, at from 80° to 200° C., preferably from 120° to 200° C., to give the 2,2-dialkylpentane 1,5-diisocyanates according to the invention and hydrogen chloride.

However, the 2,2-dialkylpentane 1,5-diisocyanates of the formula (I) are preferably prepared by pyrolysis of 2,2-dialkylpentane-1,5-diurethanes of the formula (II)

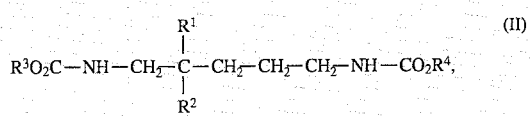

where R¹ and R² are as defined above, and R³ and R⁴ are identical or different and are linear $C_1$- to $C_{10}$-alkyl, preferably linear $C_1$- to $C_{10}$-alkyl, in particular linear $C_3$- to $C_6$-alkyl, branched $C_3$- to $C_{20}$-alkyl, preferably branched $C_3$- to $C_6$-alkyl, in particular branched $C_3$- to $C_6$-alkyl, or $C_5$- to $C_{12}$-cycloalkyl, preferably $C_5$- to $C_8$-cycloalkyl, in the presence or absence of a catalyst, a) in the gas phase at above 300° C. under reduced pressure or b) in the liquid phase at from 175° to 350° C., to give the 2,2-dialkylpentane 1,5-diisocyanates according to the invention and alcohols.

The 2,2-dialkylpentane 1,5-diurethanes of the formula (II) and -dicarbamoyl chlorides of the formula (III) are obtainable by reacting a 2,2-dialkylpentane-1,5-diamine of the formula (IV)

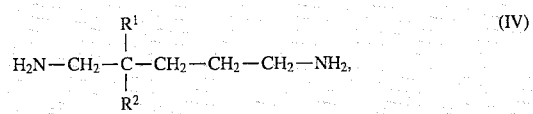

where
R¹ and R² are as defined above, in the presence or absence of a catalyst, with a) urea and a primary and/or secondary alcohol R³OH and/or R⁴OH, or b) urea and a primary and/or secondary alcohol R³OH and/or R⁴OH, where R³ and R⁴ are as defined above, in the presence of an alkyl carbamate and/or dialkyl carbonate, and, if necessary, separating off the ammonia formed, or by phosgenating a 2,2-dialkylpentane-1,5-diamine of the formula (IV) or a salt thereof, preferably a 2,2-dialkylpentane-1,5-diamine hydrochloride, in a solvent or diluent.

The novel 2,2-dialkylpentane 1,5-diisocyanates and the starting materials 2,2-dialkylpentane-1,5-diurethanes and -dicarbamoyl chlorides for their preparation and the precursors thereof can be prepared, for example, by the following processes:

2,2-Dialkylpentane-1,5-diamines of the formula (IV) are obtainable, for example, by aminating a 2,2-dialkyl-substituted 4-cyanobutanal of the formula (V)

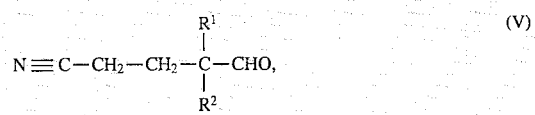

where
R¹ and R² are as defined above, in a first reaction step using excess ammonia on an acidic heterogeneous catalyst, and then hydrogenating the reaction product in a second reaction step using hydrogen in the presence of excess ammonia on a cobalt-, nickel-, ruthenium- and/or other noble metal-containing catalyst, if desired with basic components or on a basic or neutral carrier.

In an expedient process, the reaction with ammonia and the subsequent hydrogenation are carried out in two spatially separate reaction spaces.

In a first step, the 2,2-disubstituted 4-cyanobutanal (V) is reacted with excess ammonia at from 15 to 500 bar, preferably from 100 to 350 bar, and at from 20° to 150° C., preferably from 30° to 100° C. The condensation is carried out in the presence of an acidic heterogeneous catalyst. Suitable acidic heterogeneous catalysts are metal compounds having a Lewis acid or Brönstedt acid character, e.g. alumina, silica, titanium dioxide and zirconium dioxide, furthermore aluminum phosphates, e.g. aluminum phosphates, or silicates, e.g. amorphous or crystalline aluminosilicates. Preference is given to alumina, titanium dioxide zirconium dioxide and silcia, in particular alumina and titanium dioxide. The acidity of the catalyst may be increased by halide doping. Thus, for example, halogen-doped catalysts, such as chloride on alumina or chloride on titanium dioxide, are also used.

In the reaction of the 2,2-disubstituted 4-cyanobutanal (V) on an acidic heterogeneous catalyst, a weight hourly space velocity of from 0.01 to 10, preferably from 0.02 to 5, particularly preferably from 0.05 to 3 kg of 2,2-disubstituted 4-cyanobutanal per kg of catalyst and per hour is maintained. Each mole of 2,2-disubstituted 4-cyanobutanal is expediently, but not necessarily, employed with from 5 to 500 mol, preferably from 30 to 400 mol, particularly preferably from 50 to 300 mol, of $NH_3$. The reaction of the 4-cyanobutanal with ammonia may also be carried out in the presence of an inert solvent, such as an alkanol or tetrahydrofuran.

The reaction of the 2,2-disubstituted 4-cyanobutanal (V) can be carried out batchwise, but preferably continuously, for example in a pressurized reactor or a pressurized reactor cascade. In a particularly preferred embodiment, the 2,2-disubstituted 4-cyanobutanal and $NH_3$ are passed through a tubular reactor in which the catalyst is arranged in the form of a fixed bed.

The overall residence time in step 1 is determined from the weight hourly space velocity and the amount of ammonia employed and is expediently in the range from 0.5 to 120 minutes, preferably from 1 to 40 minutes, particularly preferably from 1.5 to 20 minutes.

The product obtained in this way is fed to catalytic hydrogenation in a second step using from 3 to 10,000 mol equivalents, preferably from 4.5 to 30 mol equivalents, of hydrogen, if necessary after supply of further ammonia.

The hydrogenation is preferably carried out in liquid ammonia. Each mole of 2,2-disubstituted 4-cyanobutanal (V) employed in step 1 is employed with from 5 to 500 mol, preferably from 30 to 400 mol, particularly preferably from 50 to 300 mol, of $NH_3$. If necessary, $NH_3$ can be added to the desired proportion.

The hydrogenation is generally carried out at from 60° to 150° C., preferably from 70° to 140° C., particularly preferably from 80° to 130° C., and at from 50 to 500 bar, preferably from 100 to 350 bar, particularly preferably from 150 to 300 bar.

The weight hourly space velocity is expediently in the range from 0.01 to 5 kg/[kg.h], preferably from 0.02 to 2.5 kg/[kg-h], particularly preferably from 0.05 to 2 kg/[kg.h].

In the case of continuous hydrogenation without product recycling, the overall residence time is determined from the weight hourly space velocity and the amount of ammonia employed and is in the range from 0.5 to 120 minutes, preferably from 1 to 40 minutes, particularly preferably from 1.5 to 20 minutes.

In principle, any customary hydrogenation catalyst containing nickel, cobalt, iron, copper, ruthenium or another noble metal from sub-group VIII of the Periodic Table can be employed in the hydrogenation. Ruthenium, cobalt and nickel catalysts are preferred, and ruthenium and cobalt catalysts are particularly preferred. The catalytically active metal may be employed as a pure catalyst or on a carrier. Examples of suitable carriers are alumina, titanium dioxide, zirconium dioxide, zinc oxide or magnesium oxide/alumina, preference being given to hydrogenation catalysts having basic components, such as oxides and hydroxides of alkali and alkaline earth metals. Particular preference is given to basic carriers, e.g. β-alumina or magnesium oxide/alumina. Particular preference is given to magnesium oxide/alumina containing from 5 to 40% by weight of magnesium oxide. The magnesium oxide/alumina-containing carrier may be amorphous or in the form of spinel.

The hydrogenation is particularly preferably carried out using cobalt or ruthenium with a basic component or ruthenium. These catalysts are obtained industrially in a conventional manner. Thus, for example, ruthenium on a basic carrier is obtained by applying an aqueous solution of ruthenium salt, such as ruthenium chloride or ruthenium nitrate, onto the appropriate carrier. The ruthenium concentration on the carrier is from 0.1 to 10% by weight, preferably from 0.5 to 5% by weight, particularly preferably from 1 to 4% by weight.

After drying and, if desired, after calcination at from 120° to 500° C., preferably at from 200° to 400° C., the ruthenium catalyst is activated in a stream of hydrogen at from 180° to 250° C., preferably at from 190° to 230° C., and at from 1 to 500 bar, preferably at from 20 to 300 bar, for from 1 to 20 hours, preferably for from 2 to 10 hours.

The ruthenium catalyst may also contain other metals, e.g. palladium or iron. The iron content is generally in the range from 0.5 to 5% by weight, and the palladium content is generally in the range from 0.1 to 5% by weight.

The reaction is preferably carried out continuously, for example in a pressure-tight stirred reactor or in a stirred reactor cascade. A particularly preferred embodiment employs a tubular reactor in which the mixture to be hydrogenated is passed through a fixed catalyst bed using the pool or trickle method.

It is also possible to carry out the two process steps in a single reactor in which the imination catalyst and the hydrogenation catalyst are arranged in two separate layers. In this case, the imination is expediently carried out in the presence of hydrogen.

After the hydrogenation, any excess ammonium is removed under pressure. The 2,2-disubstituted pentane-1,5-diamine, e.g. 2,2-dimethylpentane-1,5-diamine from 4-cyano-2,2-dimethylbutanal, 2-methyl-2-propylpentane- 1,5-damine from 4-cyano-2-methyl-2-propylbutanal or 2-n-butyl-2-ethylpentane-1,5-diamine from 4-cyano-2 -butyl-2-ethylbutanal, can be isolated by fractional distillation.

3-Substituted piperidines, e.g. 3,3-dimethylpiperidine from 4-cyano-2-methyl-2-propylbutanal or 3-butyl-3-ethylpiperidine from 4-cyano-2-butyl-2-ethylbutanal, are produced as by-products only to a minor extent.

The starting materials for the preparation of the 2,2-disubstituted pentane-1,5-diamines, the 2,2-di-substituted 4-cyanobutanals, are accessible from 2,2-disubstituted aldehydes and acrylonitrile.

The process described, which is the subject-matter of German Patent Application P 4010252.1, is used to prepare, in particular, the following 2,2-dialkylpentane-1,5-diamines of the formula (IV):

2-methyl-2-propylpentane-1,5-diamine, 2-ethyl-2-butylpentane-1,5-diamine, 2-methyl-2-n-nonylpentane-1,5-diamine, 1-(3-aminopropyl)-1-aminomethylcyclopentane and 1-(3-aminopropyl)-1-aminomethylcyclohexane.

To prepare the 2,2-dialkylpentane-1,5-dicarbamoyl chlorides of the formula (III), the 2,2-dialkylpentane-1,5 -diamines can be phosgenated by known methods, either directly or as salts, preferably as hydrochlorides, in a solvent or diluent. Examples of suitable solvents are toluene, xylene, chlorobenzene, dichlorobenzene and mono- and/or dicarboxylic acid esters having boiling points of from 165° to 250° C., e.g. methyl benzoate, dimethyl oxalate and/or dimethyl adipate. A solution of the 2,2-dialkylpentane- 1,5-diamine or a suspension of the corresponding salt is then reacted at from about 0° to 80° C., preferably from 10° to 50° C., with from 1 to 6 mol, preferably from 1 to 2.5 mol, in particular from 1 to 1.5 mol, of phosgene per —NH$_2$ or —NH$_2$.HCl group. The gaseous or liquid phosgene is added to the reaction mixture at such a rate that the exiting gas predominantly comprises hydrogen chloride. The 2,2-dialkylpentane-1,5-dicarbamoyl chloride is isolated by removing the solvent, for example by distillation under atmospheric or reduced pressure, and purified by known methods.

However, the 2,2-dialklpentane-1,5-dicarbamoyl chloride formed is preferably cleaved, without prior isolation, into the 2,2-dialkylpentane 1,5-diisocyanate of the formula (I) according to the invention and hydrogen chloride in one of the solvents mentioned as examples at from 80° to 200° C., preferably from 120° to 180° C.

When the phosgenation and cleavage are complete, the solvent is removed by distillation, preferably under reduced pressure, for example at from 100 to 5 mbar. It may also be advantageous to expel the hydrogen chloride and any excess phosgene from the diisocyanate solution using nitrogen or another inert gas before distilling off the solvent.

The crude 2,2-dialkylpentane 1,5-diisocyanate obtained can be purified by conventional methods, for example by distillation under reduced pressure.

Preferred embodiments involve preparing the 2,2 -dialkylpentane-1,5-diurethanes of the formula (II) according to the invention by reacting a 2,2-dialkylpentane- 1,5-diamine of the formula (IV) with a) urea and a primary and/or secondary alcohol R$^3$OH and/or R$^4$OH or, preferably, with b) urea and a primary and/or secondary alcohol R$^3$OH and/or R$^4$OH in the presence of an alkyl carbamate and/or dialkyl carbonate, and if necessary separating off the ammonia formed. The reactions can be carried out in the presence or absence of a catalyst.

However, the diurethanes of the formula II can also be obtained by other methods, for example by reacting the diamine with an alkyl carbamate as described in EP-A-18

588 or with a dialkyl carbonate, expediently in the presence of an alcohol, or by reacting the diamine with an alkyl chlorocarbonate.

In the preferred process for the preparation of the 2,2-dialkylpentane-1,5-diurethanes of the formula II, the 2,2-dialkylpentane-1,5-diamine of the formula IV is reacted with urea and alcohol in a molar ratio of from 1:1.5 to 10:2 to 50, preferably from 1:2.0 to 2.5:4 to 20, in particular from 1:2.0 to 2.3:4 to 10, at from 175° to 250° C., preferably from 180° to 230° C., in the presence or absence of a catalyst. The ammonia formed during the reaction is expediently removed immediately. In particular when a low-boiling alcohol is used, the reaction is carried out under superatmospheric pressure, set so that the reaction mixture boils at the reaction temperature used. Depending on the alcohol used, the pressure is usually from 0.1 to 60 bar, preferably from 1 to 40 bar. These reaction conditions give reaction times of from 0.5 to 50 hours, preferably from 3 to 15 hours.

Suitable alcohols $R^3OH$ and $R^4OH$ which may be identical or different, are in principle any substituted or unsubstituted, primary and/or secondary, aliphatic and/or cycloaliphatic alcohols. However, preferred alcohols are those whose boiling points are sufficiently different from the boiling point of the 2,2-dialkylpentane- 1,5-diisocyanate obtained through subsequent chemical cleavage, so that, on the one hand, very good quantitative separation of the cleavage products diisocyanate and alcohol is possible, and, on the other hand, the 2,2-dialkylpentane-1,5-diurethane formed can be evaporated essentially without decomposition.

Examples of suitable alcohols $R^3OH$ and $R^4OH$ are aliphatic, substituted or unsubstituted primary alcohols having from 1 to 20 carbon atoms, preferably from 1 to 10 carbon atoms, in particular from 3 to 6 carbon atoms, in a linear alkyl radical, secondary alcohols having from 3 to 20 carbon atoms, preferably from 3 to 10 carbon atoms, in particular from 3 to 6 carbon atoms, in a branched alkyl radical, and/or cycloaliphatic, substituted or unsubstituted alcohols having from 5 to 12 carbon atoms, in particular from 5 to 8 carbon atoms, in a substituted or unsubstituted cycloalkyl radical. Specific examples are methanol, ethanol, propanol, n-butanol, isobutanol, 2- and 3-methylbutanol, neopentyl alcohol, pentanol, 2-methylpentanol, n-hexanol, 2-ethylhexanol, n-heptanol, n-octanol, n-nonanol, n-decanol, n-dodecanol, isopropanol, sec-butanol, sec-isoamyl alcohol, cyclopentanol, cyclohexanol, 2-, 3- and 4-methylcyclohexanol and tert-butylcyclohexanol. Preference is given to methanol, ethanol, n-propanol, n-butanol, isobutanol, n-pentanol, isopentanol, n-hexanol and mixtures of aliphatic and/or cycloaliphatic alcohols and, in particular, n-propanol, n-butanol and/or isobutanol.

As stated above, the reaction of the 2,2-dialkylpentane-1,5-diamine of the formula IV with urea and alcohol can also be carried out in the presence of an alkyl carbamate and/or dialkyl carbonate. In these process variants, the dialkyl carbonate is expediently employed in an amount of from 1 to 30 mol. %, preferably from 5 to 25 mol. %, and the alkyl carbamate is expediently employed in an amount of from 1 to 20 mol. %, preferably from 5 to 18 mol. %, based on the 2,2-dialkylpentane- 1,5-diamine. However, preference is given to mixtures of dialkyl carbonates and alkyl carbamates in said mixing ratios. Preferred dialkyl carbonates and/or alkyl carbamates are those whose alkyl radicals correspond to the alkyl radical of the alcohol used.

In order to increase the reaction rate, the 2,2 -dialkylpentane-1,5-diurethane of the formula (II) can be prepared in the presence of a catalyst, which is expediently used in an amount of from 0.1 to 20% by weight, preferably from 0.5 to 10% by weight, in particular from 1 to 5% by weight, based on the weight of the 2,2-dialkylpentane-1,5-diamine. Suitable catalysts are inorganic or organic compounds which contain one or more cations, preferably a cation of a metal of group IA, IB, IIA, IIB, IIIA, IIIB, IVA, IVB, VA, VB, VIB, VIIB and VIIIB of the Periodic Table, defined as in the Handbook of Chemistry and Physics, 14th Edition, published by the Chemical Rubber Publishing Co., 23 Superior Ave. N.E., Cleveland, Ohio, for example halides, such as chlorides and bromides, sulfates, phosphates, nitrates, borates, alkoxides, phenoxides, sulfonates, oxides, oxide hydrates, hydroxides, carboxylates, chelates, carbonates and thio- or dithiocarbamates. Specific examples are the cations of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron, cobalt and nickel. Preference is given to the cations of lithium, calcium, aluminum, tin, bismuth, antimony, copper, zinc, titanium, vanadium, chromium, molybdenum, manganese, iron and cobalt. The catalysts can also be used in hydrate or ammoniacate form without any significant disadvantages being evident.

The following are examples of typical catalysts: lithium methoxide, lithium ethoxide, lithium propoxide, lithium butoxide, sodium methoxide, potassium tertbutoxide, magnesium methoxide, calcium methoxide, tin(II) chloride, tin(IV) chloride, lead acetate, lead phosphate, antimony(III) chloride, antimony(V) chloride, aluminum isobutylate, aluminum trichloride, bismuth(III) chloride, copper(II) acetate, copper(II) sulfate, copper(II) nitrate, bis(triphenylphosphinoxido)copper(II) chloride, copper molybdate, silver acetate, gold acetate, zinc oxide, zinc chloride, zinc acetate, zinc acetonyl acetate, zinc octanoate, zinc oxalate, zinc hexylate, zinc benzoate, zinc undecylate, cerium(IV) oxide, uranyl acetate, titanium tetrabutoxide, titanium tetrachloride, titanium tetraphenoxide, titanium naphthenate, vanadium(III) chloride, vanadium acetonylacetate, chromium(III) chloride, molybdenum(VI) oxide, molybdenum acetylacetonate, tungsten(VI) oxide, manganese(II) acetate, manganese(III) acetate, iron(II) acetate, iron(III) acetate, iron phosphate, iron oxalate, iron(III) chloride, iron(III) bromide, cobalt acetate, cobalt chloride, cobalt sulfate, cobalt naphthenate, nickel chloride, nickel acetate and nickel naphthenate, and mixtures thereof.

It has proven advantageous to immediately remove the resultant ammonia from the reaction mixture, for example by distillation. The apparatus used for this purpose, for example a distillation column, is operated at from 60° to 150° C., preferably from 65° to 120° C., so that coating by ammonium carbamate, formed in minimal amounts from ammonia and carbon dioxide through decomposition of urea, can be avoided.

When the reaction is complete, the alcohol, the dialkyl carbonate and/or the alkyl carbamate are expediently removed from the reaction mixture and retained for re-use in subsequent batches; in the continuous procedure, however, they are preferably recycled directly to the beginning of the diurethane preparation process.

The said compounds can be removed in one or more steps, with a two-step process being preferred. In this case, the alcohol is distilled off in the 1st step to a residual content of from 1 to 30% by weight, preferably from 2 to 15% by weight, based on the weight of the reaction mixture, and recycled to the beginning of the process.

The concentrated reaction mixture, which predominantly comprises 2,2-dialkylpentane-1,5-diurethane and possibly -oligourea-polyurethane, and the remaining alcohol, dialkyl carbonate and/or alkyl carbamate is treated in the second step with from 50 to 5,000 liters, preferably from 100 to 1000 liters, of inert gas per liter of concentrated reaction mixture and per hour in a stripping column at from 50° to 200° C., preferably from 120° to 180° C., in order to remove virtually all the remaining alcohol, dialkyl carbonate and/or alkyl carbamate. Examples of suitable inert gases for this purpose are nitrogen, carbon monoxide, noble gases and natural gas. After being stripped off, the low-boiling compounds are condensed, and, possibly after interim storage, retained for re-use in further batches. In the continuous procedure, they are preferably recycled to the beginning of the diurethane preparation process.

The 2,2-dialkylpentane-1,5-diurethane can be isolated by known methods, for example by distillation, from the reaction mixture (after distillation or preferably stripping ), which essentially comprises a 2,2-dialkylpentane-1,5-diurethane of the formula II and possibly a 2,2-dialkylpentane-oligourea-polyurethane, and, if necessary, purified further.

However, the reaction mixture is preferably pyrolyzed directly to give 2,2-dialkylpentane 1,5-diisocyanate of the formula I and alcohol.

The pyrolysis can be carried out in a conventional manner in the gas phase at above 300° C. under reduced pressure, for example in the absence of dissolved catalyst as in DE-A-24 10 505 (U.S. Pat. No. 3,870,739) or in the presence of a catalyst, for example by a method similar to that of DE-A-19 44 719 (GB 1,247,451) or in a liquid phase at from 175° to 350° C., preferably from 200° to 280° C., for example in the presence of a solvent and in the absence of a catalyst by a method similar to that of DE-A-24 21 503 (U.S. Pat. No. 3,962,302) or DE-A-25 30 001 (U.S. Pat. No. 3,919,280) or in the presence of a solvent and a catalyst, for example by a method similar to that of DE-A-26 35 490.

The 2,2-dialkylpentane-1,5-diurethane mixture possibly containing minor amounts of 2,2-dialkylpentane-oligourea-polyurethanes can, in liquid or solid form or as a suspension or solution in a solvent which is inert under the reaction conditions, be evaporated in an evaporator and pyrolyzed in a subsequent cracker.

In a preferred embodiment of the process according to the invention, the diurethane mixture, without a solvent, is introduced into the evaporator in the form of a melt at from 80° to 180° C., preferably from 100° to 150° C., by means of a metering pump.

Particularly suitable evaporators, which are operated at from 200° to 300° C., preferably from 220° to 300° C., in particular from 240° to 280° C., and at from 0.1 to 200 mbar, preferably from 5 to 100 mbar, are thin-film evaporators or fluidized bed evaporators. However, it is also possible to use any other evaporator, for example a screw evaporator, A.P. reactor (manufacturer: Krauss-Maffei), metal coil evaporator or stirred bed evaporator.

Although thin-film evaporators allow adequate supply of heat for evaporation of all the 2,2-dialkylpentane-1,5-diurethane mixture supplied, some of the diurethane mixture, together with 2,2-dialkylpentane-oligourea-polyurethane which may be present, is advantageously discharged from the reactor without evaporation, as a melt, since this achieves a significant cleaning effect on the evaporator wall. The weight ratio between evaporated and unevaporated 2,2-dialkylpentane-1,5-diurethanes can be varied within broad limits, for example from 20:80 to 90:10. The melt discharged from the evaporator is preferably recycled directly to the beginning of the diurethane preparation process, the diurethanization step.

The 2,2-dialkylpentane-1,5-diurethane vapors are introduced into the cracker and pyrolyzed batchwise or preferably continuously into 2,2-dialkylpentane 1,5-diisocyanates of the formula (I) and alcohol at above 300° C., preferably from 310° to 480° C., in particular from 350° to 450° C., and under reduced pressure, for example at from 0.1 to 200 mbar, preferably from 0.1 to 100 mbar, in particular from 1 to 50 mbar.

The cracker, which is generally in the form of a column, may have any form of cross-section. Elongated, cylindrical crackers are preferred. The internal diameter:length ratio of the reactor is generally from 1:2 to 1:1,000, preferably from 1:10 to 1:500. The cracker may be arranged vertically or horizontally and may also involve intermediate units. Preference is given to tubular furnaces, in which the tubes have an internal diameter of from 10 to 100 mm and a length of from approximately 0.5 to 5 m.

The cracking is expediently carried out in the presence of thermally stable packing elements. Suitable as such are all temperature-resistant and gas-permeable materials, e.g. beads, wool, rings and/or turnings made from charcoal, steel, brass, copper, zinc, aluminum, titanium, chromium, cobalt, nickel and/or quartz. Some of these materials, such as steel, brass, aluminum and zinc, have proven particularly successful and are therefore preferred, since they give better cracking results. It is as yet unexplained whether these are catalytic or physical effects, for example better heat transfer, or a synergistic combination of the two.

The dissociation products, which are in the vapor phase, and comprise virtually exclusively 2,2-dialkylpentane 1,5-diisocyanate and alcohol, are fed from the cracking reactor into a multistep, preferably two-step, vapor condenser. In the first condensation step, which is operated independently of the system pressure of from 0.1 to 100 mbar at from 60° to 120° C., virtually 100% of the 2,2-dialkylpentane 1,5-diisocyanate condenses out.

The second condensation step essentially involves condensation of alcohol, which is fed back to the diurethane preparation. The temperature in the second condensation step depends on the boiling point of the alcohol to be condensed and on the system pressure and is, for example, from 5° to 30° C.

The 2,2-dialkylpentane 1,5-diisocyanate of the formula I obtained in the first condensation step is usually subjected to purification distillation, after which it has a purity of greater than 99.5% by weight. The bottom product here may be fed back to the beginning of the diurethane preparation.

Depending on the choice of condensation temperatures and depending on the System pressure, varying amounts of alcohol may also be condensed in the first condensation step and diisocyanates in the second condensation step. In a preferred embodiment, the diisocyanate which has also condensed in the second condensation step is reacted with excess alcohol to give 2,2-dialkylpentane-1,5-diurethane, which is fed back, after removal of the alcohol, to evaporation and cracking. In another preferred embodiment, however, it is also possible to feed the diurethanes along with dialkyl carbonate and/or alkyl carbamate to the beginning of the diurethane preparation process.

In a similar manner, alcohol which has also condensed in the first condensation step is reacted with excess diisocyanate, and the product is fed, after removal of the diisocyanate by distillation, to evaporation and cracking or, in a preferred embodiment, under mixing with the alcohol obtained in the second condensation step, to the beginning of the diurethane preparation process.

The novel 2,2-dialkylpentane, 2,2-dialkenylpentane and 2-alkyl-2-alkenylpentane 1,5-diisocyanates and 1-(3-isocyanatopropyl)-1-isocyanatomethylcycloalkanes of the formula I are valuable starting materials for the preparation of polyurethane, polyurea and polyurethane-polyurea plastics, for example paints, coatings, sealants, adhesives, elastomers, fibers, floor coverings, foams, inter alia, by the polyisocyanate polyaddition process. Through the choice of $R^1$ and $R^2$, the physical properties e.g. boiling point, vapor pressure, polarity and solubility, can be modified and matched to the local processing conditions, and, if desired, the mechanical properties of the plastics obtained can be established, varied and improved. The 2,2-dialkenylpentane and 2-alkyl-2-alkenylpentane 1,5-diisocyanates contain, in addition to the NCO groups, at least one olefinically unsaturated reactive radical, and are therefore susceptible to subsequent reactions, in particular polymerization reactions. The diisocyanates are particularly suitable for the production of light-stable polyurethane paints and coatings.

The novel 2,2-dialkylpentane-, 2,2-dialkenylpentane- and 2-alkyl-2-alkenyl-1,5-diurethanes and 1-(3-N-carbalkoxyaminopropyl)-1-N-carbalkoxymethylcycloalkanes of the formula II are valuable end products and intermediates.

They can be employed, for example, as pesticides. As intermediates, they are used as starting components for polycondensation systems, for example by reaction with low- and/or high-molecular-weight polyhydroxyl compounds and/or polyamines for the preparation of plastics or synthetic fibers or as olefinically unsaturated monomers. They are preferably used for the preparation of diisocyanates by pyrolysis.

The novel 2,2-dialkylpentane-, 2,2-dialkenylpentane- and 2-alkyl-2-alkenylpentane-1,5-dicarbamoyl chlorides and 1-(3-N-chloroformylaminopropyl)-1-N-chloroformylaminomethylcycloalkanes are particularly suitable for the preparation of diisocyanates.

The invention is additionally illustrated by the examples below.

EXAMPLES

Example 1

A vertical tubular reactor (diameter: 16 mm, filling level: 50 cm, oil-heated twin jacket) was filled with 81.9 g (93 ml) of a catalyst containing 3% by weight of ruthenium on a magnesium oxide/alumina carrier (10% by weight of MgO, 90% by weight of $Al_2O_3$) in the form of 1 to 1.5 mm chips (catalyst preparation by pore-impregnation of a magnesium oxide/alumina carrier with aqueous ruthenium nitrate solution and drying at 120° C.). For the reduction, the catalyst was kept at 220° C. and 100 bar for 7 hours while simultaneously passing through 100 l (s.t.p.)/h of hydrogen after increasing the temperature stepwise from 100° to 220 ° C. over the course of 6 hours.

33.5 g of 2-methyl-2-propyl-4-cyanobutanal (purity: 88.9%, 29.8 g, 0.195 mol) and 1,400 ml (840 g, 49.4 mol) of liquid ammonia were pumped per hour at 250 bar and 60° C. through a tubular reactor (diameter: 16 mm, filling level: 50 cm, oil-heated twin jacket) which was arranged upstream of the hydrogenation reactor and was filled with 63.5 g (100 ml) of $TiO_2$ (anatase) in the form of 1.5 mm pellets. The product was then passed through the hydrogenation reactor from bottom to top at 250 bar and 120° C. while simultaneously passing through 100 l (s.t.p.)/h (4.5 mol) of hydrogen. After decompression to atmospheric pressure, $NH_3$ was removed by distillation. The product from 37.5 hours was separated into its components by fractional distillation on a 30 cm packed column (3 mm glass rings), giving 277.0 g of 3-methyl-3-propylpiperidine (b.p.=46° C./2 mm Hg) and 842.1 g of 2-methyl-2-propylpentane-1,5-diamine (b.p.= 78°–81° C./2 mm Hg). The yield of diamine was 72.9% of theory.

Example 2

Example 1 was repeated using 2-butyl-2-ethyl-4-cyanobutanal as a starting material. 33.6 g of 2-ethyl-2-butyl-4-cyanobutanal (purity: 89.0%, 29.9 g, 0.165 mol) and 1,344 ml (806 g, 47.4 mol) of liquid ammonia were pumped per hour at 250 bar and 60° C. through the imination reactor. The product was then passed through the hydrogenation reactor from bottom to top at 250 bar and 120° C. while simultaneously passing through 100 l (s.t.p.)/h (4.5 mol) of hydrogen. After decompression to atmospheric pressure, $NH_3$ is removed by distillation. The product from 16.7 hours was separated into its components by fractional distillation on a 30 cm packed column (3 mm glass rings), giving 166.8 g of 3-butyl-3-ethylpiperidine (b.p.=73° to 75° C./2 mm Hg) and 267.5 g of 2-ethyl-2-butylpentane-1,5-diamine (b.p.=105° C./2 mm Hg). The yield of diamine was 52.1% of theory.

Example 3

158 g of 2-methyl-2-propylpentane-1,5-diamine, prepared as in Example 1, 126 g of urea and 370 g of butanol were refluxed at 230° C. for 4 hours and 9 bar in a 1 liter stirred autoclave fitted with pressure column and pressure regulation valve, while releasing ammonia. 590 g of a clear liquid whose analysis by gel permeation chromatography indicated a conversion into 2-methyl-2-propyl-1,5-bis(butoxycarbonylamino)pentane of 95% were obtained. Excess butanol and a small amount of butyl carbamate were removed by distillation, leaving 355 g of a viscous liquid, which was employed in the pyrolysis without further purification. Column chromatography on silica gel gave pure 2-methyl-2-propyl-1,5-bis(butoxycarbonylamino)pentane as a colorless, viscous oil.

| C,H,N-analysis: | C | H | N |
| --- | --- | --- | --- |
| calculated | 63.65 | 10.68 | 7.81 |
| found | 63.68 | 10.72 | 7.78 |

Example 4

A cracking apparatus comprising a thin-layer evaporator, a cracking reactor (cylindrical V2A-steel tube with a capacity of about 1 liter, filled with zinc-plated steel packing) and a two-step vapor condensation apparatus was evacuated to 5 mbar. 350 g of the 2-methyl-2-propyl-1,5-bis(butoxycarbonylamino)pentane obtained as in Example 3 were introduced into the thin-layer evaporator at 260° C. over the course of 2 hours, 315 g evaporating and 35 g running off. The diurethane vapors passed into the cracking reactor which had a mean temperature of 400° C. The exiting cracking gases were subjected to fractional condensation in a downstream two-step condesation apparatus at from 65° to 18° C. 205 g of crude diisocyanate, which was purified by vacuum distillation (head temperature 105° to 107° C./0.5 mbar), were produced in the first condenser. 157.3 g (53% yield) of 2-methyl-2-propylpentane 1,5-diisocyanate having a purity of 98% were obtained.

Example 5

186 g of 2-ethyl-2-butylpentane-1,5-diamine, prepared as in Example 2, 126 g of urea and 444 g of butanol were refluxed at 230° C. for 5 hours and 10 bar in a 1 liter stirred autoclave fitted with pressure column and pressure regulation valve, while releasing ammonia. 670 g of a clear liquid whose analysis by gel permeation chromatography indicated a conversion into 2-ethyl-4-butyl-1,5-bis(butoxycarbonylamino)pentane of 98% were obtained. Excess butanol and a small amount of butyl carbamate were removed by distillation, leaving 390 g of a viscous liquid, which was employed in the pyrolysis without further purification. Column chromatography on silica gel gave pure 2-ethyl-2-butyl-1,5-bis(butoxycarbonylamino)pentane as a colorless, viscous oil.

| C,H,N-analysis: | C | H | N |
|---|---|---|---|
| calculated | 65.25 | 10.95 | 7.25 |
| found | 65.27 | 10.99 | 7.20 |

Example 6

The cracking was carried out in the apparatus described in Example 4. 550 g of the 2-ethyl-2-butyl-1,5-bis(butoxycarbonylamino)pentane obtained as in Example 5 were introduced over the course of 3 hours into the thin-layer evaporator heated to 280° C. and evacuated to from 8 to 9 mbar, 502 g evaporating and 48 g running off. The mean temperature in the cracking reactor was 400° C. 340 g of crude diisocyanate were collected in the condenser operated at 85° C. This crude product was pre-purified by distillation in a thin-film evaporator (oil temperature 160° C./0.2 mbar) and distilled again under reduced pressure at 113° C./0.5 mbar. 223 g (70% yield) of 2-ethyl-2-butylpentane 1,5-diisocyanate having a purity of 99% were obtained.

Example 7

15.8 g of 2-methyl-2-propylpentane-1,5-diamine were added dropwise with vigorous stirring and ice cooling to a mixture, cooled to 0° C., of 200 g of o-dichlorobenzene and 60 g of phosgene. When the addition was complete, the resultant suspension was warmed to 130° C., and phosgene was passed through the reaction mixture at this temperature for 2.5 hours. After the mixture had been cooled, the excess phosgene was expelled by means of a vigorous stream of nitrogen, the o-dichlorobenzene was removed by distillation under reduced pressure at 10 mbar, and the residue was distilled at from 107° to 110° C./0.5 mbar. 15.2 g (73% yield) of 2-methyl-2-propylpentane 1,5-diisocyanate were obtained.

We claim:

1. A 2,2-dialkylpentane 1,5-diisocyanate of the formula (I)

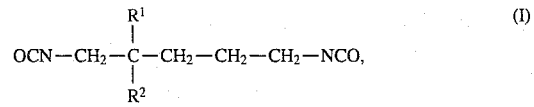

wherein $R^1$ and $R^2$ are identical or different and are linear alkyl having from 2 to 12 carbon atoms, branched alkyl having from 3 to 12 carbon atoms, linear alkenyl having from 2 to 12 carbon atoms or branched alkenyl having from 4 to 12 carbon atoms.

* * * * *